United States Patent [19]
Ohmizu et al.

[11] Patent Number: 5,831,091
[45] Date of Patent: Nov. 3, 1998

[54] PROCESS FOR PREPARING ACETOXYAZETIDINONE DERIVATIVE AND INTERMEDIATE THEREOF

[75] Inventors: Hiroshi Ohmizu, Kyoto; Masahiko Seki, Nagaokakyo, both of Japan

[73] Assignee: Tanabe Seiyaku Co., Ltd., Osaka, Japan

[21] Appl. No.: 743,834

[22] Filed: Nov. 5, 1996

[30] Foreign Application Priority Data

Nov. 17, 1995 [JP] Japan ................................. 7-299524

[51] Int. Cl.[6] ................................. C07D 205/00
[52] U.S. Cl. ..................... 544/92; 540/357; 540/362; 544/50; 544/287; 560/170; 567/253
[58] Field of Search ................................. 544/92

[56] References Cited

U.S. PATENT DOCUMENTS

| 2,943,087 | 6/1960 | Ohnacker et al. | 544/92 |
| 3,652,571 | 3/1972 | Sturm et al. | 544/92 |
| 3,719,688 | 3/1973 | Teichert et al. | 544/92 |

FOREIGN PATENT DOCUMENTS

| 0337637 | 10/1989 | European Pat. Off. . |
| 0371875 | 6/1990 | European Pat. Off. . |
| 0485218 | 5/1992 | European Pat. Off. . |
| 0509821 | 10/1992 | European Pat. Off. . |
| 0632037 | 1/1994 | European Pat. Off. . |
| 0597423 | 5/1994 | European Pat. Off. . |
| 0635488 | 1/1995 | European Pat. Off. . |
| 5239019 | 2/1992 | Japan . |

OTHER PUBLICATIONS

Ziegler et al. Chem. Abstr vol. 68 Entry 105 126, 1968.
Miyake et al Chem Abstr vol. 125 Entry 2793 26, 1996.
Seki et al Chem Abstr vol 125 Entry 195 241, 1996.
Seki et al Chem Abstr vol. 125 Entry 86 358, 1996.
Seki et al. Tetrahedron Lett. vol. 37 pp. 5565–5568, 1996.
David A. Evans et al, "Adol Addition Reactions of Chiral Crotonate Imides", Tetrahedron Letters, vol. 27, pp. 4957–4960, 1986.
David A. Evans et al, The Asymmetric Synthesis of B–Lactam Antibiotic—IV.[1] A Formal Synthesis of Thienamycin., Tetrahedron Letters, vol. 27, pp. 4961–4964, 1986.
Seki et al., "A Novel Synthesis of a Key Intermediate for Penems and Carbapenems Utilizing Lipase–Catalyzed Kinetic Resolution", Tetrahedron: Asymmetry, vol. 7 No. 5, pp. 1241–1244, 1996.

Primary Examiner—Donald G. Daus
Attorney, Agent, or Firm—Browdy and Neimark

[57] ABSTRACT

An N-[2-(1-hydroxyethyl)-3-oxopropyl]amine compound of the formula [III]:

[Chemical structure III]

wherein Ring B represents a benzene ring which may be substituted; W represents oxygen atom or sulfur atom; Y represents oxygen atom, sulfur atom or N $R^0$, $R^0$ represents hydrogen atom or a substituent; Z represents a substituted methylene group which contains at least one chiral center; $R^5$ represents an aralkyloxycarbonyl group or an alkoxycarbonyl group; $R^6$ represents hydrogen atom, an aralkyl group, an acyloxy group, a tri-substituted silyloxy group or an alkoxy group; or both of $R^5$ and $R^6$ bond at their termini and combine with the adjacent nitrogen atom to form phthalimido group, and a process thereof are disclosed. Said compound [III] is useful as a starting compound of β-lactam antibacterial agents.

11 Claims, No Drawings

PROCESS FOR PREPARING ACETOXYAZETIDINONE DERIVATIVE AND INTERMEDIATE THEREOF

TECHNICAL FIELD

The present invention relates to a process for preparing an acetoxyazetidinone derivative which is useful as a starting compound of β-lactam antibacterial agents, and intermediate thereof.

PRIOR ART

A (3R, 4R)-4-acetoxy-2-azetidinone derivative of the formula [I];

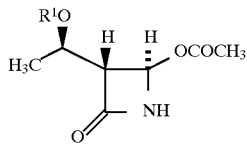

wherein $R^1$ is a protecting group for hydroxy group, is useful as a starting compound of carbapenem antibacterial agents, for example, 2-(pyrrolidin-2-on- 4-ylthio)-6-(1-hydroxyethyl)-1-methylcarbapen-2-em-3-carboxylic acid. (European Patent Publication No. EP-337637-A)

As a process for preparing the said (3R, 4R)-4-acetoxy-2-azetidinone derivative [I], there has been known a process which comprises the steps of:
(i) subjecting 2-(N-benzoylaminomethyl)-3-oxobutanoic acid methyl ester to asymmetric reduction in the presence of a chiral ruthenium-phosphine complex under hydrogen atmosphere, to give (2S, 3R)-2-(N-benzoylaminomethyl)-3-hydroxybutanoic acid methyl ester,
(ii) hydrolyzing (2S, 3R)-2-(N-benzoylaminomethyl)-3-hydroxybutanoic add methyl ester, followed by neutralization and lactamyzation, to give (1'R, 3S)-3-hydroxyethylazetidin-2-one,
(iii) protecting the hydroxy group of the product to give the compound of the formula [II]:

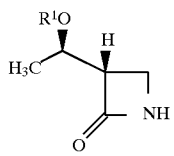

wherein $R^1$ represents the same as defined above, and
(iv) reacting the compound [II] with acetic acid and an oxidizing agent in the presence of a ruthenium compound as a catalyst. (European Patent Publication No. EP-371875-A)

There has been known another process which comprises the steps of:
(i) reducing 2-(phthalimidomethyl)acetoacetic acid benzyl ester to catalytic hydrogenation in the presence of a chiral catalyst under hydrogen atmosphere, to give (2S, 3R)-3-hydroxy-2-(phthalimidomethyl)butanoic acid benzyl ester,
(ii) reacting the product obtained above with tert-butyldimethylsilyl chloride, followed by treatment with hydrazine, to give (2S, 3R)-2-aminomethyl-3-(tert-butyldimethylsilyloxy)butanoic acid benzyl ester,
(iii) subjecting (2S, 3R)-2-aminomethyl-3- (tert-butyldimethylsilyloxy)butanoic acid benzyl ester to catalytic hydrogenation in the presence of the palladium catalyst under hydrogen atmosphere to give (2S, 3R)-2-aminomethyl-3-(tert-butylmethylsilyloxy)butanoic acid, and (iv) lactamyzing the product to give the compound [II]. (Japanese Patent Provisional Publication No. JP05239019-A)

However, these processes need an expensive chiral ruthenium-phosphine complex as a catalyst in the asymmetric reduction, so they are unsatisfactory for industrial scale production from the viewpoint of cost and operation.

BRIEF DESCRIPTION OF THE INVENTION

An object of the present invention is to provide a novel process and novel intermediate compounds for preparing a (3R, 4R)-4-acetoxy-2-azetidinone derivative which is useful as a starting compound of β-lactam antibacterial agents.

DETAILED DESCRIPTION OF THE INVENTION

As a result of intensive studies on a process for preparing a (3R, 4R)-4-acetoxy-2-azetidinone derivative, it has been found that an N-[2-(1-hydroxyethyl)-3-oxopropyl]amine compound of the formula [III]:

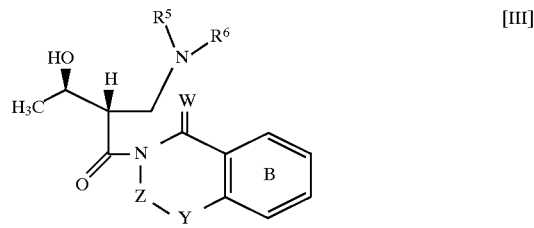

wherein Ring B represents a benzene ring which may be substituted; W represents oxygen atom or sulfur atom; Y represents oxygen atom, sulfur atom or N $R^0$, $R^0$ represents hydrogen atom or a substituent; Z represents a substituted methylene group which contains at least one chiral center; $R^5$ represents an aralkyloxycarbonyl group or an alkoxycarbonyl group; $R^6$ represents hydrogen atom, an aralkyl group, an acyloxy group, a tri-substituted silyloxy group or an alkoxy group; or both of $R^5$ and $R^6$ bond at their termini and combine with the adjacent nitrogen atom to form phthalimido group, can be obtained stereoselectively and effectively, and can be used as a key intermediate of a (3R, 4R)-4-acetoxy-2-azetidinone derivative.

According to the present invention, the N-[2-(1-hydroxyethyl)-3-oxopropyl]amine compound of the formula [I]:

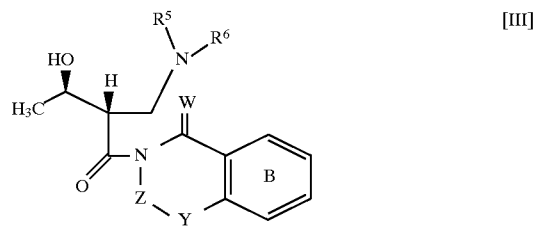

wherein Ring B, W, Y, Z, $R^5$ and $R^6$ represent the same as difined above, can be prepared by reacting an N-(3-oxopropyl)amine compound of the formula [IV];

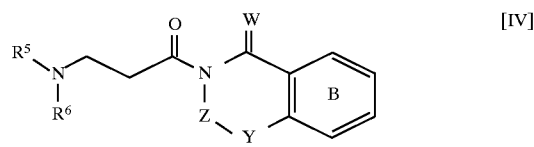

wherein Ring B, W, Y, Z, $R^5$ and $R^6$ represent the same as defined above, with acetaldehyde or a reactive derivative thereof.

In the present invention, the substituents on Ring B may be any one which does not take part in the reaction of the compound [IV] with acetaldehyde or a reactive derivative thereof. For example, said substituents include a halogen atom, a lower alkyl group, a lower alkoxy group, an aryl group, nitro group, a lower alkylthio group, di-lower alkylamino group and the like, and the benzene ring may have one to four substituent(s) which are same or different.

When Y is N $R^0$, example of $R^0$ includes a lower alkyl group, an acyl group and an aralkyloxycarbonyl group. The acyl group may be an aliphatic acyl group such as a lower alkanoyl group.

Examples of the substituent(s) of the substituted methylene group (Z) include a lower alkyl group, an aryl group, or an alkylene group having more than two carbon atoms and having one or more substituent(s) (e.g. a lower alkyl group) to make Z chiral. For example, such group Z includes groups represented by the following formula;

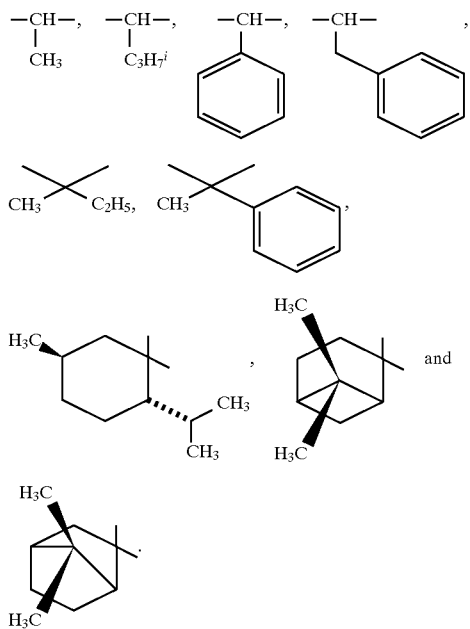

[The symbol "$C_3H_7^i$" is iso-propyl.]

Among these groups, preferred group is a group of the formula;

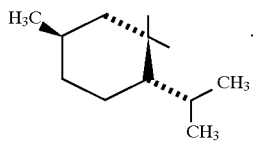

Example of the substituents on silicon atom of the tri-substituted silyloxy group R6 includes a straight or branched lower alkyl group (e.g. methyl group, ethyl group, iso-propyl group and tert-butyl group) and phenyl group. These substituents are the same or different.

Preferred compounds [III] and [IV] are those wherein Ring B is a benzene ring which may be substituted, W is oxygen atom, Y is oxygen atom, Z is a substituted methylene group which contains at least one chiral center, $R^5$ is a phenyl-substituted lower alkoxycarbonyl group, $R^6$ is a lower alkanoyloxy group, or both of $R^5$ and $R^6$ bond at their termini and combine with the adjacent nitrogen atom to form phthalimido group.

Among the above compounds, more preferred ones are those wherein Ring B is unsubstituted benzene ring; W is oxygen atom; Y is oxygen atom; Z is an alkylene-substituted methylene group, in which alkylene moiety is substituted by at least one lower alkyl group and which contains at least one chiral center; $R^5$ is a phenyl-substituted lower alkoxycarbonyl group; $R^6$ is a lower alkanoyloxy group; or both of $R^5$ and $R^6$ bond at their termini and combine with the adjacent nitrogen atom to form phthalimido group.

The reaction of the compound [IV] with acetaldehyde or a reactive derivative thereof can be carried out in an appropriate solvent. Further, the reaction can be carried out preferably in the presence of a metal catalyst, more preferably in the presence of a metal catalyst and a base. Example of the reactive derivative of acetaldehyde includes the corresponding acetal.

The example of the "metal catalyst" used in the present invention includes the metal compound of the formula [V]:

$$LJ_nQ_m \quad [V]$$

wherein L represents a metal atom; J represents a halogen atom; Q represents a lower alkyl group, a lower alkoxy group, phenoxy group, a substituted phenoxy group or cyclopentadienyl group, each of n and m represents 0, 1, 2, 3, 4 or 5, and the sum of n and m is equal to the valence of L. When n or m is two or more, J or Q may be the same or different.

Examples of the metal atom (L) include titanium. (Ti), zinc (Zn), tin (Sn), boron (B), zirconium (Zr), aluminum (Al), magnesium (Mg) and the like. Among them, preferred example is titanium (Ti).

Examples of the metal catalyst include titanium catalysts such as $TiCl_4$, $TiCl_3(OCH_3)$, $TiCl_3(OC_2H_5)$, $TiCl_3(OC_3H_7^n)$, $TiCl_3(OC_3H_7^i)$, $TiCl_3(OC_4H_9^n)$, $TiCl_3(OC_4H_9^i)$, $TiCl_3(OC_4H_9^s)$, $TiCl_3(OC_4H_9^t)$, $TiCl_2(OCH_3)_2$, $TiCl_2(OC_2H_5)_2$, $TiCl_2(OC_3H_7^n)_2$, $TiCl_2(OC_3H_7^i)_2$, $TiCl(OC_3H_7^i)_3$ or $TiCl_2(OC_4H_9^n)_2$; zinc catalysts such as $ZnCl_2$ or $ZnI_2$; tin catalysts such as $SnCl_4$ or $Sn(OTf)_2$; boron catalysts such as $BOTf(C_4H_9^n)_2$; zirconium catalysts such as $ZrCl_4$, $ZrCl_3(OCH_3)$, $ZrCl_3(OC_2H_5)$, $ZrCl_3(OC_3H_7^n)$, $ZrCl_3(OC_3H_7^i)$, $ZrCl_3(OC_4H_9^n)$, $ZrCl_3(OC_4H_9^i)$ or $ZrCl_3(OC_4H_9^t)$; aluminum catalysts such as $AlCl_3$, $Al(OCH_3)_3$, $Al(OC_2H_5)_3$, $Al(OC_3H_7^i)_3$, $AlCl_2CH_3$, $AlCl(CH_3)_2$, $Al(CH_3)_3$, $AlCl_2C_2H_5$, $AlCl(C_2H_5)_2$ or $Al(C_2H_5)_3$; magnesium catalysts such as $Mg(OC_2H_5)_2$, $MgI_2$ or $MgClO_4$; and the like. [The symbol "Tf" is tolyflate. The symbols "$C_3H_7^n$", "$C_3H_7^i$", "$C_4H_9^n$", "$C_4H_9^i$", "$C_4H_9^s$" and "$C_4H_9^t$" are normal-propyl, iso-propyl, normal-butyl, iso-butyl, secondary-butyl and tertiary-butyl, respectively.]

Among the above metal catalysts, preferred metal catalyst is a titanium catalyst, for example, $TiCl_4$ or $TiCl(OC_3H_7^i)_3$.

Examples of the base include an amine compound and silazane compound. The examples of the amine compound include secondary amines such as a di-lower alkylamine (e.g., dimethylamine, diethylamine, diisopropylamine, dicyclohexylamine and the like), an N-alkylaniline (e.g., N-methylaniline and the like) and a heterocyclic amine (e.g., piperidine, pyrroridine, 2,2,6,6-tetramethylpiperidine, morpholine, piperadine and the like); tertiary amines such as a tri-lower alkyl amine (e.g., diisopropylethylamine, diisopropylmethylamine, triethylamine and the like), an N,N-di-alkylaniline (e.g., N,N-dimethylaniline and the like), a heterocyclic amine (e.g., 1-ethylpiperidine, 1-methylmorpholine, 1-ethylpyrroridine, 1,4diazabicyclo-[2.2.2]octane, 1,8-diazabicyclo[5.4.0]undec-7-ene and the like) and a diamine (e.g., N,N,N',N'-tetramethylethylenediamine and the like); pyridine compounds such as an alkylpyridine (e.g., α-picoline, β-picoline, γ-picoline, 2,3-lutidine, 2,4-lutidine, 2,5-lutidine, 2,6-lutidine, 3,4-lutidine, 3,5-lutidine, 2,4,6-collidine and the like), a dialkylaminopyridine (e.g., dimethylaminopyridine and the like) and a benzene-fused pyridine (e.g., quinoline and the like); and the like. The examples of "silazane compound" include an alkali metal hexa-lower alkyldisilazane such as sodium hexamethyldisilazane, lithium hexamethyldisilazane or the like.

Among the above mentioned base, preferred ones are the tertiary amine and the alkali metal hexa-lower alkyldisilazane, more specially triethylamine and sodium hexamethyldisilazane.

Any conventional inert solvent may be used in the reaction. Examples of the solvent include tetrahydrofran, dichloromethane, dichloroethane, dimethoxyethane, toluene, dimethylformamide and hexamethylphosphorictriamide, more preferably, tetrahydrofran and dichloromethane.

It is preferred to carry out the reaction at a temperature of −78° C. to 10° C., more preferably at a temperature of −78° C. to −10° C.

The compound [III] thus obtained can be converted into the compounds which can be used as synthetic intermediates for a (3R, 4R)-4-acetoxy-2-azetidinone derivative [I], by the following processes A, B or C.

[Process A]

A compound of the formula [III-a]:

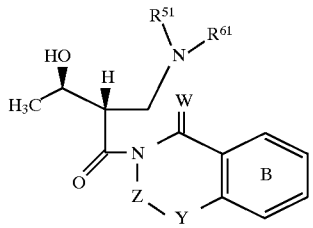
[III-a]

wherein Ring B, W, Y and Z represent the same as defined above; $R^{51}$ represents an aralkyloxycarbonyl group or an alkoxycarbonyl group; $R^{61}$ represents hydrogen atom or an aralkyl group; or both of $R^{51}$ and $R^{61}$ bond at their termini and combine with the adjacent nitrogen atom to form phthalimido group, is reacted with a compound of the formula [VI]:

$R^1X$ [VI]

wherein $R^1$ represents the same as defined above, X represents a reactive residue, to give a compound of the formula [VII]:

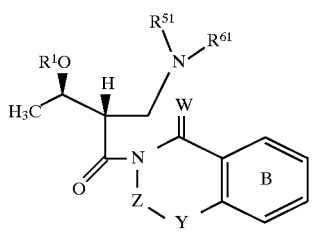
[VII]

wherein Ring B, W, Y, Z, $R^1$, $R^{51}$ and $R^{61}$ represent the same as defined above. Then, the compound [VII] thus obtained is reacted with a compound of the formula [VIII]:

$R^2OM^1$ [VIII]

wherein $R^2$ represents a lower alkyl group which may be substituted by an aryl group and $M^1$ represents an alkali metal, to give a compound of the formula [IX]:

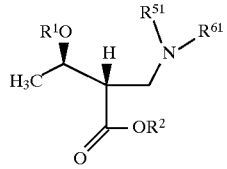
[IX]

wherein $R^1$, $R^2$, $R^{51}$ and $R^{61}$ represent the same as defined above.

[Process B]

The compound [III-a] is reacted with a compound of the formula [X]:

$R-NH_2$ [X]

wherein R represents methyl group or amino group, and a compound of the formula [XI]:

$M^2OOH$ [XI]

wherein $M^2$ represents an alkali metal, to give (2S)-3-amino-2-((1R)-1-hydroxyethyl)propionic acid.

[Process C]

A compound of the formula [III-b]:

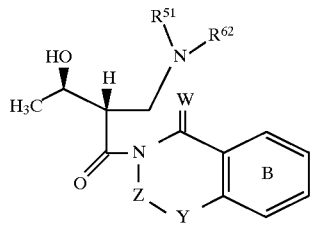
[III-b]

wherein $R^{52}$ represents an aralkyloxycarbonyl group or an alkoxycarbonyl group, $R^{62}$ represents an acyloxy group, a tri-substituted silyloxy group or an alkoxy group, Ring B, W, Y and Z represent the same as defined above, is reacted with the compound [VI], to give a compound of the formula [XII]:

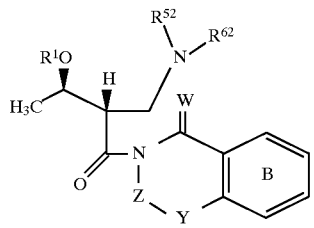
[XII]

wherein Ring B, W, Y, Z, $R^1$, $R^{52}$ and $R^{62}$ represent the same as defined above. Then, the compound [XII] obtained above is reacted with a compound of the formula [VIII-a]:

$R^{21}OM^1$ [VIII-a]

wherein $R^{21}$ represents a lower alkyl group and $M^1$ represents the same as defined above, to give a compound of the formula [XIII]:

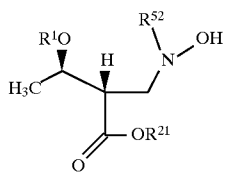

wherein $R^1$, $R^{21}$ and $R^{52}$ represent the same as defined above, and the compound [XIII] is subjected to catalytic hydrogenation to give a compound of the formula [XIV]:

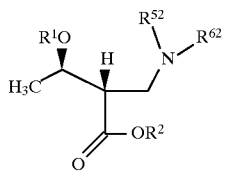

wherein $R^1$ and $R^{21}$ represent the same as defined above.

The reaction of the compound [III-a] or [III-b] with the compound [VI] can be conducted by a conventional method. Examples of the reactive residue X are a halogen atom, tri-fluoromethanesulfonyloxy group and the like.

Protecting group $R^1$ for hydroxy group may be any conventional protecting group for hydroxy group. Preferred protecting group is a tri-substituted silyl group in which three substituents on silicon atom are the same or different and are a straight or branched lower alkyl group or phenyl group. Example of such tri-substituted silyl group are trimethylsilyl group, triethylsilyl group, tert-butyldimethylsilyl group, methyldiisopropylsilyl group, tert-butyldiphenylsilyl group, triphenylsilyl group or the like.

It is preferred to carry out the reaction in an appropriate solvent such as dichloromethane, in the presence of a base such as 2,6-lutidine, under cooling or at room temperature.

The reaction of the compound [VII] with the compound [VIII] and the reaction of the compound [XII] with the compound [VIII-a] can be conducted by a conventional method. The alkali metal (M') of the compound [VIII] includes, for example, sodium, lithium or the like. It is preferred to carry out the reaction in a solvent such as tetrahydrofran or the like under cooling or at room temperature.

The reaction of the compound [III-a] with the compoundws [X] and [XI] can be conducted by a conventional method. Example of an alkali metal ($M^2$) of the compound [XI] is sodium, lithium or the like. It is preferred to carry out the reaction in a solvent such as-methanol or the like under cooling or at room temperature.

Catalytic hydrogenation of the compound [XIII] can be conducted by a conventional method. Example of the catalyst is a palladium catalyst such as palladium on activated carbon, and example of the solvent is a lower alkanol such as methanol. It is preferred to carry out the reaction at a temperature of $-20°$ C. to $150°$ C.

The starting compound [IV] of the present invention is novel, and can be prepared, for example, by reacting an acid chloride of the compound of the formula:

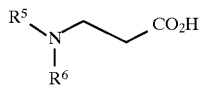

wherein $R^5$ and $R^6$ represents the same as defined above, with a compound of the formula [XV]:

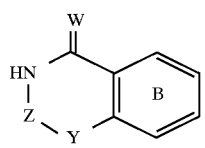

wherein Ring B, W, Y and Z represent the same as defined above, in the presence of a base (e.g., diisopropylethylamine) and a catalyst (e.g., copper(I) chloride) under heating.

A compound of the formula [IV-b]:

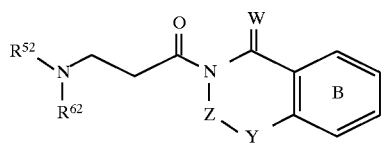

wherein Ring B, W, Y, Z, $R^{52}$ and $R^{62}$ represent the same as defined above, can be prepared by the steps of:

(i) reacting the compound [XV] with an acryloyl halide in the presence of a base (e.g., diisopropylethylamine) to give a compound of the formula [XVI]:

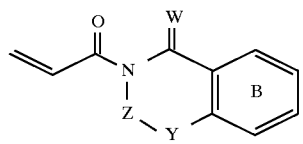

wherein Ring B, W, Y and Z represent the same as defined above, and (ii) reacting the compound [XVI] with a compound of the formula [XVII]:

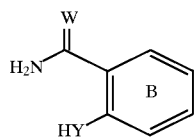

wherein $R^{52}$ and $R^{62}$ represent the same as defined above, in the presence of a base (e.g., sodium hydride) and a catalyst (e.g., copper(I) chloride) under heating.

The compound [XV] is also novel and can be prepared, for example, by reacting a compound of the formula:

wherein Ring B, W and Y represent the same as defined above, with the compound of the formula:

wherein Z represents the same as defined above, in an appropriate solvent (e.g., toluene) in the presence of an acid (e.g., para-toluenesulfonic acid) or a base (e.g., pyrrolidine) under heating.

The compounds [IX] and [XIV] and (2S)-3-amino-2-((1R)-1-hydroxyethyl)propionic acid obtained by the above processes can be converted into a (3R, 4R)-4-acetoxy-2-azetidinone derivative [I], which is useful as a starting compound of an antibacterial agent, by a conventional method, for example, by the process disclosed in European Patent Publication No. EP-371875-A, European Patent Publication No. EP485218-A, European Patent Publication No. EP-509821-A or Japanese Patent Provisional Publication No. JP05239019-A. For example, the (3R,4R)-4-acetoxy-2-azetidinone derivative [I] can be prepared by the steps of:
(i) reacting the compound [IX] with hydrazine to give a compound of the formula [XVIII]:

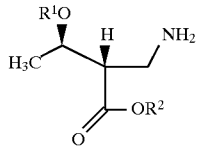

[XVIII]

wherein $R^1$ and $R^2$ represent the same as defined above,
(ii) subjecting the compound [XVIII] to catalytic hydrogenation in the precence of a palladium catalyst (e.g., a palladium on activated carbon) to give a compound of the formula [XIX]:

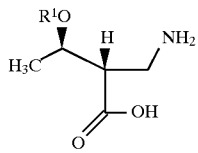

[XIX]

wherein $R^1$ represents the same as defined above,
(iii) lactamyzing the compound [XIX] to give the compound [II], and
(iv) introducing acetoxy group into the compound [II].

The compound [II] can be also prepared by reacting the compound [XIV] or the compound [XVIII] with a Grignand agent (e.g., ethyl magnesium bromide).

Further, the compound [II] can be prepared by the steps of:
(i) reacting (2S)-3-amino-2-((1R)-1-hydroxyethyl)propionic acid with a lactamyzing agent (e.g., N-tert-butyl-2-benzothiazolsulfenamide(II), triphenylphosphine) to give (1'R, 3S)-3-(1'-hydroxyethyl)azetidin-2-one, and
(ii) reacting the above product with the compound [VI].

In the processes A, B and C, the compound [XV] can be recovered and then recycled. From the viewpoint of recovery of the compound [XV], the process C is preferable.

Throughout the specification and claims, the terms "alkyl" and "alkoxy" include ones having 1 to 20 carbon atoms, preferably ones having 1 to 6 carbon atoms, more preferably 1 to 4 carbon atoms, respectively. The term "alkylene" includes one having 1 to 20 carbon atoms, preferably one having 1 to 6 carbon atoms, more preferably 3 to 5 carbon atoms. The terms "lower alkyl" and "lower alkoxy" includes ones having 1 to 6 carbon atoms, preferably ones having 1 to 4 carbon atoms, respectively. The term "lower alkanoyl" includes one having 2 to 6 carbon atoms, preferably ones having 2 to 4 carbon atoms. The term "aryl" includes a phenyl which may be substituted and a naphthyl which may be substituted. The terms "halogen atom" or "halide" include fluorine, chlorine, bromine, iodine or the like:

EXAMPLE

Example 1

(1) A mixture of salicyl amide (16.5 g), pyrrolidine (8.35 ml) and (−)-menthone (17.1 g) in toluene (200 ml) was refluxed under continuous removal of water for 6 hr. The mixture was cooled, washed, dried and evaporated. The residue was purified by silica-gel column chromatography (chloroform:n-hexane:ethyl acetate=5:5:1) to afford 24.2 g of (2'S, 5'R)-2'-isopropyl-5'-methyl- spiro[2,3-dihydro-4H-1,3-benzoxazin-2,1'-cyclohexan-4-one (2S isomer:2R isomer=2:1). Into a solution of the above product in N-methylpyrolidone (132 ml) was added 1,8-diazabicyclo[5.4.0]undec-7-ene (1.32 ml). The mixture was stirred at 25° C. for 12 hr, and then stirred at −10° C. for 24 hr. The mixture was quenched by a 10% aqueous citric acid, and the mixture was extracted with ethyl acetate. The extract was washed, dried and evaporated to afford 23.7 g of (2'S, 5'R)-2'-isopropyl-5'-methyl-spiro[2,3-dihydro-4H-1,3-benzoxazine-2,1'- cyclohexane]-4-one (2S isomer:2R isomer=14:1).

2S isomer; M.p. 80°–82° C. $[\alpha]_D^{23}$–82.3° (c=1.10, methanol). 2R isomer; M.p. 156°–158° C. $[\alpha]_D^{23}$+63.8° (c=1.157, methanol).

(2) A mixture of the product of Example 1-(1) (2S isomer:2R isomer=14:1) (27.4 g), acryloyl chloride (9.75 ml), triethylamine (16.7 ml) and copper(I) chloride (500 mg) in toluene (200 ml) was stirred at 50° C. for 3 hr. The mixture was extracted with ethyl acetate, and the extract was washed, dried and evaporated. The residue was purified by silica-gel column chromatography (n-hexane:ethyl acetate=10:1) to afford 26.8 g of (2S, 2'S, 5'R)-3-acryloyl-2'- isopropyl-5'-methyl-spiro[2,3-dihydro-4H-1,3-benzoxazine-2,1'-cyclohexanel-4-one.

IR(KBr)vmax: 1706,1681, 1609 cm$^{-1}$ MS m/z:327(M$^+$)

(3) Into a solution of O-acetyl-N-benzyloxycarbonylhydroxyamine (1.94 g) in dimethylformamide (28 ml) was added sodium hydride (62.4 % in oil) (37 mg) at −10° C., and the mixture was stirred at −10° C. for 30 min. Into the mixture was added a solution of the product of Example 1-(2) (3.04 g) in dimethylformamide (28 ml) at −60° C., and the mixture was gradually warmed to 25° C. for 1.5 hr. The mixture was poured into water, and extracted with diethylether. The extract was washed, dried, and evaporated. The residue was purified by silica-gel column chromatography (n-hexane:ethyl acetate= 10:1) to afford 5.0 g of (2S, 2'S, 5'R)-3-(3-(O-acetyl-N-benzyloxycarbonylhydroxyamino)propionyl)-2'-isopropyl- 5'-methyl-spiro[2,3-dihydro-4H-1,3-benzoxazine-2,1'-cyclohexane]-4-one.

IR(Nujol)vmax: 1798, 1716, 1687, 1610 cm$^{-1}$ SIMS m/z: 537(M$^+$+1)

(4) Into a solution of the product of Example 1-(3) (537 mg) in dichloromethane (6 ml) was added dropwise titanium (IV) tetrachloride (1M in dichloromethane) (2 ml) at −70° C. to −60° C., and the mixture was stirred at −70° C. to −60° C. for 15 min. Into the mixture was added dropwise triethylamine (202 mg) at −70° C. to −60° C., and the mixture was stirred at −70° C. to −60° C. for 40 min. Then, into the mixture was added dropwise a solution of acetaldehyde (0.54 ml) in dichloromethane (1.2 ml) at −70° C. to −60 ° C. The mixture was gradually warmed to 0° C. for 2 hr, and the mixture was poured into water, and extracted with dichloromethane. The extract was washed, dried, and evaporated. The residue was purified by silica-gel column chromatography (n-hexane:ethyl acetate=4:1) to afford 500 mg of (2'S, 5'R)-3-[(2S)-3-(O-acetyl-N- benzyloxycarbonylhydroxyamino)-2-((1R)-1-hydroxyethyl)propionyl)-2'- isopropyl-5'-methyl-spiro[2,3-dihydro-4H-1,3-benzoxazine-2,1'-cyclohexane]-4-one.

IR(Nujol)vmax: 3540, 1797, 1690, 1610 cm$^{-1}$ SIMS m/z: 581 (M$^+$+1)

Example 2

(1) A mixture of β-alanine (89 g) and phthalic anhydride (148 g) was heated at 180° C. to 190° C. for 30 min. The mixture was cooled to 60° C. and ethyl acetate (500 ml) was added, and the mixture was stirred at 0° C. for 1 hr. n-Hexane is added to the reaction mixture and the reactant crystals were collected filteration to afford 219.5 g of 3-phthalimidopropionic acid in colorless crystals. M.p. 149°–151° C.

(2) Into a mixture of the product of Example 2-(1) (6.6 g) and dichloromethane (60 ml) was added dropwise thionylchloride (2.2 ml). The mixture was stirred at 50° C. for 30 min, and then evaporated. Into the residue was added toluene (60 ml), the product of Example 1-(1) (5.39 g) and copper(I) chloride (60 mg), and the mixture was stirred at 70° C. for 5 hr. After cooling, ethyl acetate was added into the mixture. The mixture was washed, dried and evaporated. The residue was purified by silica-gel column chromatography (n-hexane:ethyl acetate=7:1) to afford 8.16 g of (2S, 2'S, 5'R)-3-(3- phthalimidopropionyl)-2'-isopropyl-5'-methyl-spiro[2,3-dihydro-4H-1,3-benzoxazine-2,1'-cyclohexane]-4-one in colorless crystals.
M.p. 154°–155° C. $[\alpha]_D^{25}$+32.8° (c=0.375, methanol)

(3) Into a solution of the product of Example 2-(2) (300 mg) in dichloromethane (3 ml) was successively added dropwise titanium(IV) chloride (1M in dichloromethane) and triethylamine (0.18 ml) at –70° C. to –60° C., and the mixture was stirred at –70° C. to –60° C. for 30 min. Into the mixture was added dropwise a solution of acetaldehyde (0.93 ml) in dichloromethane (0.5 ml) at –70° C. to –60° C., and the mixture was stirred at –70° C. to –60° C. for 2.5 hr. The mixture was warmed to –10° C. to 0° C. and stirred for 2 hr. The mixture was poured into water, and extracted with dichloromethane. The extract was washed, dried and evaporated. The residue was purified by silica-gel column chromatography (n-hexane:ethyl acetate=4:1) to afford 292 mg of (2'S, 5'R)-3- [(2S)-3-phthalimido-2-((1R)-1-hydroxyethyl)propionyl]-2'-isopropyl-5'-methyl- spiro[2,3-dihydro-4H-1,3-benzoxazine-2,1'-cyclohexane]-4-one in colorless crystals.
M.p. 141°–142° C. $[\alpha]_D^{25}$-24.5° (c=0.31, methanol)

Example 3

Into a solution of the product of Example 2-(2) (4.27 g) in tetrahydrofran (65 ml) was added dropwise sodium hexamethyldisilazane (1M in tetrahydrofran) (9.9 ml) at –78° C., and the mixture was stirred at –78° C. for 1 hr. Into the mixture was added chlorotitanium triisopropoxide (1M in hexane) (9.9 ml) at –78° C., and the mixture was stirred at –78° C. for 100 min. Into the mixture was added acetaldehyde (3 ml) at –78° C., and the mixture was gradually warmed to 5° C. for 2 hr. The mixture was diluted with phosphate buffer (pH 7) (100 ml) and ethyl acetate (100 ml). The reactant white precipitates were removed by filteration using celite. The organic layer of the filtrate was separated and washed, dried and evaporated. The residue was purified by silica-gel column chromatography (n-hexane:ethyl acetate=3:1) to afford 4.768 g of (2'S, 5'R)-3-[(2S)-phthalimido-2-((1R)-1-hydroxyethyl)propionyl]-2'-isopropyl-5'-methyl-spiro[2,3-dihydro-4H-1,3-benzoxazine-2,1'-cyclohexane]-4-one in colorless crystals.
M.p. 141°–142° C. $[\alpha]_D^{25}$-24.5° (c=0.31, methanol)

Example 4

(1) Into a solution of the product of Example 3 (1.6 g) in dichloromethane (30 ml) were added tert-butyldimethylsilyltriflate (1.25 g) and 2,6-lutidine (1.0 g) at 5° C., and the mixture was stirred at 5° C. for 10 min. The mixture was poured into water and extracted. The extract was washed, dried and evaporated. The residue was purified by silica-gel column chromatography (n-hexane:ethyl acetate=12:1) to afford 1.95 g of (2'S, 5'R)-3-[(2S)-3-phthalimido-2-((1R)- 1-tert-butyldimethylsilyloxyethyl)propionyl]-2'-isopropyl-5'-methyl-spiro[2,3- dihydro-4H-1,3-benzoxazine-2,1'-cyclohexane]-4-one in colorless crystals.
M.p. 119°–120° C. $[\alpha]_D^{25}$+51.8 ° (c=0.31, methanol)

(2) Into a solution of benzyl alcohol (1.51 ml) in tetrahydrofran (57 ml) was added n-butyl lithium (1.6 M in hexane) (7.25 ml) at –60° C., and the mixture was warmed to 25° C. Into the solution of benzyloxy lithium thus obtained was added the product of Example 4-(1) (6.0 g) at –78° C., and the mixture was stirred at 3° C. for 17 hr. The mixture was diluted with water and ethyl acetate. The organic layer was washed, dried and evaporated. The residue was purified by silica-gel column chromatography (chloroform:n-hexane:ethylacetate= 10:1:0.1) to afford 2.57 g of (2S)-phthalimido-2-[(1R)-1-tert-butyldimethylsilyloxyethyl]-propionic acid benzyl ester in colorless oil.
IR (KBr) vmax: 1770,1718 cm$^{-1}$ SIMS m/z: 468 (M$^+$+1) $[\alpha]_D^{25}$+15.2° (c=0.99, methanol)

Example 5

Into a solution of the product of Example 2-(3) (2 g) in methanol (6 ml) was added dropwise a 4% methylamine solution (in methanol) (0.79 ml) at 0° C. to 10° C., and the mixture was stirred for 55 min. Into the mixture was successively added dropwise a 31% aqueous hydrogen peroxide in water (0.93 ml) and a 2M aqueous sodium hydroxide (3.85 ml) at 0° C. to 10° C., and the mixture was stirred at 0° C. to 10° C. for 15 min. Into the mixture was added sodium persulfate (1.07 g), and the mixture was stirred at 0° C. to 10° C. for 10 min, then at 25° C. for 2.5 hr. The mixture was filtered to remove insoluble materials, and the filtrate was evaporated. Into the residue was added water, and the mixture was washed with chloroform. The aqueous layer was lyophilized, and the residue was purified by cation exchange resin (IRA-120) column chromatography to afford 386 mg of (2S)-3-amino-2-((1R)-1-hydroxyethyl)propionic acid.
IR(Nujol)vmax: 2971, 1584 cm$^{-1}$ SIMS m/z: 133 (M$^+$)

Besides the washing solutions were combined, and evaporated. The residue was purified by silica-gel column chromatography (n-hexane:ethylacetate=4:1) to recover 397 mg of (2'S, 5'R)-2'-isopropyl-5'-methyl- spiro[2,3-dihydro-4H-1,3-benzoxazine-2,1'-cyclohexane]-4-one.

Example 6

(1) A mixture of the product of Example 1-(4) (1.72 g), tert-butyldimethylsilylchloride (671 mg), imidazole (909 mg) and dimethylformamide (10 ml) was stirred at 25° C. for 17 hr. The mixture was poured into water, and extracted with ethylacetate. The extract was washed, dried and evaporated. The residue was purified by silica-gel column chromatography (n-hexane:ethylacetate=10:1) to afford 2 g of (2'S, 5'R)-3-[(2S)-3-(N-acetoxy-N-benzyloxycarbonylamino)-2- ((1R)-1-tert-butyldimethylsilyloxyethyl)propionyl]-2'-isopropyl-5'-methyl- spiro[2,3-dihydro-4H-1,3-benzoxazine-2,1'-cyclohexane]-4-one.
IR(Nujol)vmax: 1800,1690,1610 cm$^{-1}$ SIMS m/z: 695 (M$^+$+1)

(2) Into methanol (1 ml) was added n-butyl lithium (1.6M in hexane) (0.17 ml) at 0° C. to afford a solution of lithium methoxide. The solution was dropwise added to a solution of the product of Example 6-(1) (186 mg) in methanol (6 ml) at −10° C., and the mixture was stirred at −10° C. for 1 hr. The reaction was quenched by adding a 10% aqueous citric acid, and the mixture was evaporated. The residue was extracted with chloroform, and the extract was dried and evaporated. The residue was purified by silica-gel column chromatography (n-hexane:ethylacetate=4:1) to afford 100 mg of (2S)-3-(N- hydroxy-N-benzyloxycarbonylamino)-2-((1R)-1-tert-butyldimethylsilyloxy- ethyl)propionic acid methyl ester.
IR(Nujol)vmax: 3270, 1740, 1706 cm$^{-1}$ SIMS m/z: 412 (M$^+$+1)

Besides, 74 mg of (2'S, 5'R)-2'-isopropyl-5'-methyl-spiro [2,3-dihydro-4H- 1,3-benzoxazine-2,1'-cyclohexane]-4-one was recovered.

(3) A mixture of the above product (21 mg), 10 % palladium on activated carbon (50% wet, 2 mg) and methanol (5 ml) was subjected to catalytic hydrogenation at 25° C. under hydrogen atmosphere (3.5 atm) for 3 hr. The mixture was filtered, and the filtrate was evaporated. The residue was purified by silica-gel column chromatography (chloroform:methanol=10:1) to afford 14 mg of (2S)-3-amino-2-((1R)-1-tert-butyldimethylsilyloxyethyl)propionic acid methyl ester.
IR(Nujol)vmax: 1737 cm$^{-1}$ SIMS m/z: 262 (M$^+$+1)

Reference Example 1

(1) A mixture of (2S)-3-phthalimido-2-((1R)-1-tert-butyldimethylsilyloxyethyl)propionic acid benzyl ester (1.12 g), hydrazine monohydrate (612 mg) and ethanol (20 ml) was stirred at 25° C. for 17 hr. The reactant crystals were filtered off and the filtrate was evaporated. The residue was suspended in hexane and filtered. The filtrate was evaporated, and the residue was purified by silica-gel column chromatography (chloroform:methanol=40:1) to afford 642.2 mg of (2S)-3-amino-2-((1R)-1-tert-butyldimethylsilyloxyethyl) propionic acid benzyl ester in colorless oil.
IR(KBr)vmax: 1732 cm$^{-1}$ SIMS m/z: 338 (M$^+$+1) $[\alpha]_D^{25}$−24.2° (c=1.2, methanol)

(2) A mixture of the product of Reference Example 1-(1) (390 mg), 10% palladium on activated carbon (50% wet, 770 mg) and methanol (30 ml) was subjected to catalystic hydrogenation at 25° C. under hydrogen atmosphere (3.5 atm) for 1 hr. The mixture was warmed to 50° C. and then filtered. The filtrate was evaporated, and adding acetone and ether were added to the residue. The crystalline precipitates were collected by filteration to afford 200 mg of (2S)-3- amino-2-((1R)-1-tert-butyldimethylsilyloxyethyl)propionic acid in colorless crystals.
M.p. 192°–194° C.

(3) Into a solution of the product of Reference Example 1-(2) (70 mg) in acetnitrile (57 ml) was added triphenylphosphine (75 mg) and 2,2'-dipyridyl disulfide (75 mg) at 25° C. The mixture was stirred at 60° C. for 5 hr and further stirred at 40° C. for 8 hr. The mixture was evaporated and the residue was purified by silica-gel column chromatography (n-hexane:ethylacetate=4:1) to afford 49 mg of (1'R, 3S)-3-(1'-tert-butyldimethylsilyloxyethyl)azetidin-2-one in colorless crystals.
M.p. 66°–67° C. $[\alpha]_D^{25}$−68.7° (c=0.6, methanol)

(4) Into a mixture of the product of Reference Example 1-(3) (100 mg), sodium acetate (29 mg) and ruthenium (III) chloride trihydrate (18.3 mg) were added ethylacetate (14 ml) and acetic acid (0.7 ml), and the mixture was stirred under oxygen atmosphere at 40° C. for 30 min. Into the mixture was added acetaldehyde (0.15 ml), and the mixture was stirred at 40° C. for 3 hr. The mixture was poured into a 10% aqueous sodium sulfide (60 ml), and extracted twice with ethyl acetate. The extracts were combined, washed, dried and evaporated. The residue was purified by silica-gel column chromatography (n-hexane:ethylacetate=3:1) to afford 155 mg of (1'R, 3R, 4R)-4-acetoxy-3-(4'-tert- butyldimethylsilyloxyethyl)-2-azetidinone in colorless crystals.
M.p. 104°–107° C. $[\alpha]_D^{25}$+29.3° (c=0.9, methanol)

Reference Example 2

Into a solution of the product of Reference Example 1-(1) (100 mg) in tetrahydrofran (2 ml) was added dropwise ethyl magnesium bromide (1M in tetrahydrofran) (1.38 ml) at −15° C. for 1 hr, and the mixture was stirred at −10° C. for 2 hr and warmed to 25° C. for 30 min. The mixture was poured into water and extracted with ethyl acetate. The extract was washed, dried and evaporated. The residue was purified by silica-gel column chromatography (n-hexane:ethyl acetate=4:1) to afford 31 mg of (1'R, 3S)-3-(1'-tert- butyldimethylsilyloxyethyl)azetidin-2-one in colorless crystals.
M.p. 66°–67° C. $[\alpha]_D^{25}$−68.7° (c=0.6, methanol)

What is claimed is:

1. A compound of the formula [XX]:

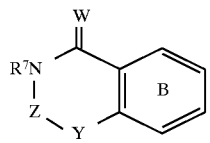

wherein Ring B represents benzene ring which may be substituted by one substituent selected from the group consisting of a lower alkyl group, a lower alkoxy group, an aryl group, a lower alkylthio group and a di-lower alkylamino group, W represents oxygen atom or sulfur atom; Y represents oxygen atom; Z is a group represented by the formula:

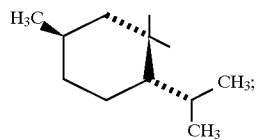

$R^7$ represents hydrogen atom, acryloyl group, a group represented by the formula:

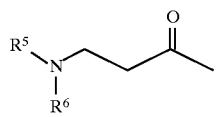

wherein $R^5$ represents a phenyl-substituted lower alkyloxycarbonyl group or an alkoxycarbonyl group; $R^6$ represents hydrogen atom, a phenyl-substituted alkyl group, a lower alkanoyloxy group, a tri- (straight or branched lower alkyl) silyloxy group, a tri-phenylsilyloxy group or an alkoxy group; or both $R^5$ and R6 bond at their termini and combine with the adjacent nitrogen atom to form phthalimido group, or a group represented by the formula:

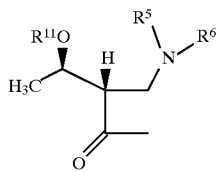

wherein $R^{11}$ represents hydrogen atom or a protecting group for hydroxy group; $R^5$ and $R^6$ represent the same as defined above.

2. The compound according to claim 1, wherein $R^7$ is hydrogen atom.

3. The compound according to claim 1, wherein $R^7$ is an acryloyl group.

4. The compound according to claim 1, wherein $R^7$ is a group represented by the formula:

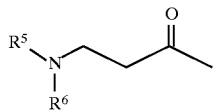

wherein $R^5$ represents a phenyl-substituted lower alkoxycarbonyl group or an alkoxycarbonyl group; $R^6$ represents hydrogen atom, a phenyl-substituted alkyl group, a lower alkanoyloxy group, a tri- (straight or branched lower alkyl) silyloxy group, a tri-phenylsilyloxy group or an alkoxy group; or both of $R^5$ and $R^6$ bond at their termini and combine with the adjacent nitrogen atom to form phthalimido group.

5. The compound according to claim 1, wherein $R^7$ is a group represented by the formula:

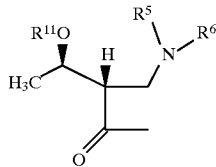

wherein $R^{11}$ represents hydrogen atom or a protecting group for hydroxy group; $R^5$ represents a phenyl-substituted lower alkyloxy carbonyl group or an alkoxycarbonyl group; $R^6$ represents hydrogen atom, a phenyl-substituted alkyl group, a lower alkanoyloxy group, a tri- (straight or branched lower alkyl) silyloxy group, a tri-phenylsilyloxy group or an alkoxy group; or both of $R^5$ and $R^6$ bond at their termini and combine with the adjacent nitrogen atom to form phthalimido group.

6. (2'S,5'R)-2'-isopropyl-5'-methyl-spiro[2,3- dihydro-4H-1,3-benzoxazine-2,1'-cyclohexane]-4-one.

7. A compound of the formula [XX]:

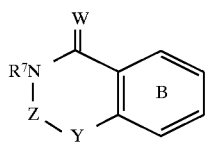

[XX]

wherein Ring B represents an unsubstituted benzene ring, W represents oxygen atom or sulfur atom; Y represents oxygen atom; and Z is a group represented by the formula:

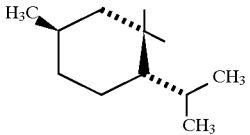

$R^7$ represents hydrogen atom, acryloyl group, and a group represented by the formula:

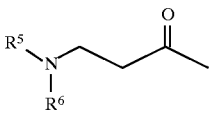

wherein $R^5$ represents a phenyl-substituted lower alkyloxycarbonyl group or an alkoxycarbonyl group; $R^6$ represents hydrogen atom, a phenyl-substituted alkyl group, a lower alkanoyloxy group, a tri-(a straight or branched lower alkyl) silyloxy group, a triphenylsilyloxy group or an alkoxy group; or both of $R^5$ and $R^6$ bond at their termini and combine with the adjacent nitrogen atom to form phthalimido group, or a group represented by the formula:

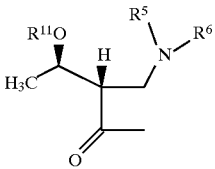

wherein $R^{11}$ represents hydrogen atom or a protecting group for hydroxy group; $R^5$ and $R^6$ represent the same as defined above.

8. The compound according to claim 7, wherein $R^7$ is hydrogen atom.

9. The compound according to claim 7, wherein $R^7$ is an acryloyl group.

10. The compound according to claim 7, wherein $R^7$ is a group represented by the formula:

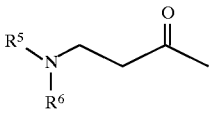

wherein $R^5$ represents a phenyl-substituted lower alkyloxycarbonyl group or an alkoxycarbonyl group; $R^6$ represents hydrogen atom, a phenyl-substituted alkyl group, a lower alkanoyloxy group, a tri-(a straight or branched lower alkyl) silyloxy group, a triphenylsilyloxy group or an alkoxy group; or both of $R^5$ and $R^6$ bond at their termini and combine with the adjacent nitrogen atom to form phthalimido group.

11. The compound according to claim 7, wherein $R^7$ is a group represented by the formula:

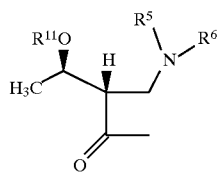

wherein $R^{11}$ represents hydrogen atom or a protecting group for hydroxy group; $R^5$ represents a phenyl-substituted lower alkyloxycarbonyl group or an alkoxycarbonyl group; $R^6$ represents hydrogen atom, a phenyl-substituted alkyl group, a lower alkanoyloxy group, a tri-(a straight or branched lower alkyl)silyloxy group, a triphenylsilyloxy group or an alkoxy group; or both of $R^5$ and $R^6$ bond at their termini and combine with the adjacent nitrogen atom to form phthalimido group.

* * * * *